United States Patent [19]
Grimberg

[11] Patent Number: 6,165,482
[45] Date of Patent: Dec. 26, 2000

[54] GASTROINTESTINAL DRUG COMPOSITION

[76] Inventor: Georges Serge Grimberg, 39 Quai d'Orsay, Paris 75007, France

[21] Appl. No.: 09/005,023

[22] Filed: Jan. 12, 1998

[30] Foreign Application Priority Data

Feb. 7, 1997 [FR] France .................................. 97 01410

[51] Int. Cl.⁷ .................................................. A01N 25/08
[52] U.S. Cl. .......................... 424/405; 424/406; 424/407; 424/421; 424/497; 424/498; 424/125; 514/63; 514/529; 514/770; 514/772.3
[58] Field of Search ..................... 424/405, 406, 424/407, 408, 421, 441, 475–476, 482, 485, 490, 497, 498, 125; 514/63, 529, 770, 772.3, 819, 820

[56] References Cited

U.S. PATENT DOCUMENTS

| | | | |
|---|---|---|---|
| 2,934,472 | 4/1960 | May | 464/125 |
| 3,325,402 | 6/1967 | Erskine | 424/418 |
| 3,901,976 | 8/1975 | Roth et al. | 426/69 |
| 3,921,636 | 11/1975 | Zaffaroni | 424/468 |
| 3,937,801 | 2/1976 | Lippmann | 514/530 |
| 4,243,678 | 1/1981 | Krastinat | 514/563 |
| 4,822,765 | 4/1989 | Nishimura | 502/418 |
| 5,047,244 | 9/1991 | Sanvordeker et al. | 424/435 |
| 5,332,427 | 7/1994 | Hayashi et al. | 106/18.32 |
| 5,413,788 | 5/1995 | Edwards et al. | 424/409 |
| 5,547,656 | 8/1996 | Unger | 424/9.4 |
| 5,612,054 | 3/1997 | Garwin | 424/441 |
| 5,691,014 | 11/1997 | Andersen et al. | 428/34.5 |

FOREIGN PATENT DOCUMENTS

| | | |
|---|---|---|
| 12127/33 | 4/1933 | Australia . |
| 2390953 | 1/1979 | France . |
| 197512 | 12/1975 | Japan . |

*Primary Examiner*—Neil S. Levy
*Attorney, Agent, or Firm*—Browdy and Neimark

[57] ABSTRACT

A composition for treating the gastrointestinal tract comprising a porous insoluble absorbent in which the pores of the insoluble absorbent are clogged by a coating material which causes the insoluble absorbent to adhere to the gastrointestinal lining. Active ingredients, including antacids, antibiotics, antibacterial agents, platelet inhibitors, antispasmodics, and soporifics, can be mixed with or absorbed into the composition.

21 Claims, No Drawings

GASTROINTESTINAL DRUG COMPOSITION

FIELD OF THE INVENTION

The present invention relates to gastrointestinal drug compositions based on a porous insoluble absorbent wherein the insoluble absorbent is coated with a material which covers the openings of the pores of the insoluble absorbent. These compositions can be used alone or in combination with other pharmaceutical compositions.

BACKGROUND OF THE INVENTION

Gastrointestinal drugs are used to treat functional, alimentary, bacteriological, and medical conditions and symptoms. Gastrointestinal drugs are often used in combination with antispasmodics, tranquilizers, peripheral and cerebral vasodialators, analgesics, vasoprotectors, antibiotics, and the like.

Dimethylpolysiloxane, or simethicone, has been used to treat flatulence and stomach and intestinal gas. Charcoal has traditionally been used as an absorbent for these gases. Nevertheless, the therapeutic action of charcoal, except for its ability to clear the body of poison when the charcoal is given in high amounts, has not heretofore been recognized. Activated charcoal has been used as an antidote for poisons, by absorbing poisons in the body. However, about 100 mg of charcoal cannot absorb one liter of gas, nor can it selectively absorb toxins or other disruptive compounds in a body. The therapeutic activity of dimethylpolysiloxane has also been the subject of much discussion.

SUMMARY OF THE INVENTION

It is an object of the present invention to provide a gastrointestinal composition based upon insoluble absorbent or other [porous] insoluble absorbent which has been coated by a substance which adheres to the insoluble absorbent but does not contain anything to cause disintegration of the insoluble absorbent. This coated insoluble absorbent has a therapeutic action completely different from that conventionally attributed to the insoluble absorbent.

According to the present invention, the pores of an insoluble absorbent are clogged by a coating material. The therapeutic activity of the coated insoluble absorbent thus is quite different from absorption of gases and toxins or degassing the gastrointestinal tract.

According to the present invention, the new gastrointestinal composition comprises an insoluble absorbent which is coated to cover the pores of the insoluble absorbent. The coating can be dimethylpolysiloxane and/or isopropyl myristate or any other compound which fills in the pores of the insoluble absorbent but which does not aid disintegration of the insoluble absorbent. The pharmaceutical composition acts by adhering to the gastrointestinal lining, where it is available over an extended period of time.

The pharmaceutical composition based on coated insoluble absorbent can be combined with other active ingredients, which may optionally be coated. A pharmaceutical composition based on coated insoluble absorbent according to the present invention can contain several hundred milligrams, up to one gram, of active ingredients, for example, antibiotics, antacids, and the like.

Prior to being coated according to the present invention, the insoluble absorbent can be associated with, i.e., mixed with, small quantities (of the order of tens of milligrams) of active ingredients, such as platelet inhibitors, antispasmodics, or soporifics. These active ingredients are either mixed with the insoluble absorbent so that they are absorbed by the insoluble absorbent or, preferably, are dissolved or suspended in a liquid to be mixed with the insoluble absorbent. After these liquids are mixed with the activated insoluble absorbent, the liquids are evaporated, forming an activated insoluble absorbent with the active ingredient absorbed in the pores of the insoluble absorbent.

The coated porous insoluble absorbent of the present invention can be used in conjunction with conventionally used active ingredients. The coated insoluble absorbent can be mixed with ingredients such as antacids, antiseptics, antibiotics, etc., for oral administration, in any combination that is effective for the condition being treated.

Although the present application uses charcoal as the preferred insoluble absorbent, clay or other insoluble, relatively inert, porous material which has been coated in a similar fashion can be used for pharmaceutical compositions according to the present invention. For purposes of the present invention, adsorption and absorption may be used to describe the same phenomenon.

DETAILED DESCRIPTION OF THE INVENTION

According to the present invention, charcoal or other inert, insoluble absorptive material is coated with a coating material which causes the absorbent material to adhere to the lining of the gastrointestinal tract. The coating covers the pores of the insoluble absorbent and causes the composition to adhere to the walls of the stomach or vessel to which it is added, either in an aqueous medium or in a gastric medium. Thus, the composition of the present invention adheres to the lining of the stomach, intestines, or esophagus. If an active ingredient is associated with the coated absorbent, the active ingredient remains in contact with the gastrointestinal lining for a longer period than would be possible if the active ingredient were merely administered orally and quickly passes through the gastrointestinal tract.

The insoluble absorbent is coated with the coating material, e.g., dimethylpolysiloxane or isopropyl myristate. While the insoluble absorbent can be coated with up to approximately its own weight of coating material, in a preferred embodiment the ratio of the insoluble absorbent to the coating material is from about 3:2 to about 4:1. In the most preferred embodiment, the insoluble absorbent is coated with coating material in an approximately 3:1 ratio by weight. That is, approximately 140 mg of insoluble absorbent is coated with approximately 45 mg of coating material. In general, depending upon the active ingredient used, the active ingredient comprises from about 0.05% to about 80% by weight of the composition.

EXAMPLE 1

A therapeutic dose according to the present invention comprised the following:

| | |
|---|---|
| Activated charcoal | 140 mg |
| Dimethylpolysiloxane | 45 mg |

This dose was administered in a capsule to a healthy volunteer. Endoscopic analysis revealed that the product adhered to the gastric lining of the volunteer. Alternatively, when this dose of activated charcoal and dimethylpolysiloxane was administered as a suspension in water, endoscopic analysis also revealed that this suspension adhered to the esophageal and the gastric lining.

Accordingly, to deliver medication or absorptive material to the esophagus and stomach, the coated absorbent can be administered in an aqueous or other liquid suspension. For delivery to the intestines, the composition should be administered encased in an enteric coating.

EXAMPLE 2

A therapeutic dose was prepared from charcoal and isopropyl myristate as follows:

| | |
|---|---|
| Activated charcoal | 140 mg |
| Isopropyl myristate | 45 g |

This dose of activated charcoal coated with isopropyl myristate was administered in a capsule to a healthy volunteer. Endoscopic analysis revealed that the product adhered to the gastric lining of the volunteer. Alternatively, when this dose of activated charcoal coated with isopropyl myristate was administered as a suspension in water, endoscopic analysis also revealed that this suspension adhered to the esophageal and the gastric lining.

EXAMPLE 3

Activated charcoal, 140 mg, uncoated, was administered to a healthy volunteer. Endoscopic analysis revealed that the charcoal agglomerated in pieces, and did not adhere to the gastric lining as one agglomerated mass. When 140 mg of activated charcoal was placed into a separating funnel containing water, the charcoal dispersed and regrouped in several agglomerates, rather than in one agglomerated mass as with the coated charcoal.

The pharmaceutical composition of the present invention comprising an absorbent coated with a coating material such as dimethylpolysiloxane or isopropyl myristate, is useful for treating abdominal pains in general. The composition is also useful in treating dyspeptic troubles associated with symptoms of slow digestion, postprandial discomfort, nausea, vomiting, flatulence, meteorism, diarrhea and/or constipation. The results found in treating patients suffering from the above conditions were excellent, which results are attributed to the fact that the composition adheres to the esophageal, gastric, or intestinal lining for a time sufficient to accomplish the purpose for which it was administered.

For patients suffering from a spastic colon, capsules of charcoal coated with dimethylpolysiloxane are administered. Within ten minutes after administration of the capsules, even while the contents of the capsule are still in the stomach, the colon is relaxed. The adherence of this product to the gastric surface gives order to the gastrointestinal tract. This has nothing to do with the absorbent power of the charcoal, or the anti-gas ability of the dimethylpolysiloxane, as this effect is not observed when these components are administered separately, i.e., the charcoal is not coated with the dimethylpolysiloxane. It was also noted that people who took this capsule have lost 2 to 4 kg in weight.

EXAMPLE 4

One hundred forty mg of activated charcoal was coated with 40 mg of dimethylpolysiloxane and mixed with 250 mg of amoxicillin. Two volunteers were treated in eight day intervals with 500 mg of amoxicillin and then with two capsules containing a mixture of 250 mg amoxicillin and 140 mg of activated charcoal coated with 40 mg of dimethylpolysiloxane. The quantity of amoxicillin absorbed taken with or without the coated charcoal was the same. However, with the coated charcoal, there is a repartition in time of the quantity of amoxicillin remaining in the body, which is, because of this time delay, very favorable to the activity of the amoxicillin.

EXAMPLE 5

Magnesium oxide is a well-known antacid which works by neutralizing stomach acid. However, use of magnesium oxide alone has disadvantages in that the magnesium oxide does not remain in the stomach for very long, so that its antacid activity is not available to neutralize the stomach acid for an extended period of time. However, if magnesium oxide is mixed with charcoal coated with dimethylpolysiloxane or isopropyl myristate, magnesium oxide has a remarkably larger antacid capacity because the combination of magnesium oxide and coated charcoal adhere to the gastric lining. Because the magnesium oxide is in contact with the stomach acid for an extended period of time, its antacid capacity is greatly increased.

In formulating an antacid medication, it is also possible to include a compound which destroys *Helicobacter pylori* in order to treat gastrointestinal ulcers as well as merely to treat excess stomach acid production. Products used to treat *H. pylori*, iodine, or other antibiotics or antiseptics, can be mixed with the coated charcoal for delivery to the stomach. By virtue of the coated insoluble absorbent's adhering to the gastric lining, the antibiotic or antiseptic remains in the milieu of the stomach for an extended period of time so that there is a greater opportunity for the active ingredients to act to destroy the *H. pylori*.

EXAMPLE 6

Acetylsalicylic acid is a known platelet inhibitor. To lengthen the time that the acetylsalicylic acid is in contact with the gastric lining, a solution of acetylsalicylic acid in ethanol is used to moisten activated charcoal. The ethanol is evaporated to form a charcoal which contains acetylsalicylic acid absorbed in the pores. This charcoal containing acetylsalicylic acid is then coated with a coating according to the present invention, e.g., dimethylpolysiloxane or isopropyl myristate.

Capsules were prepared containing 140 mg of activated charcoal containing 20 mg of acetylsalicylic acid in the pores thereof. This charcoal was then coated with dimethylpolysiloxane, and administered to a healthy volunteer. It was found that the platelet inhibition of this product was excellent, and makes it possible greatly to decrease the quantity of acetylsalicylic acid administered to decrease platelet activity.

As noted above, the insoluble absorbent can either be mixed with an active ingredient or an active ingredient can be absorbed into the pores of the insoluble absorbent by mixing the insoluble absorbent with a solution or suspension of the active ingredient, permitting the active ingredient to penetrate into the pores of the insoluble absorbent, and then evaporating the liquid. This treated insoluble absorbent is then coated with a coating material that enables the insoluble absorbent to adhere to the gastrointestinal lining, such as dimethylpolysiloxane or isopropyl myristate.

Compositions within the scope of the present invention include combinations of insoluble absorbent with a coating that causes the insoluble absorbent charcoal to adhere to the gastrointestinal lining, along with optional other active ingredients. The active ingredients are present in amounts effective to achieve the intended purpose of the active ingredient(s). Determination of the effective amounts is within the skill of the art. However, it has been found that lower quantities of active ingredients are generally required than for active ingredients which are not associated with the insoluble absorbent coated as in the present invention, because active ingredients associated with the insoluble absorbent coated according to the present invention remain in the gastrointestinal tract longer, and therefore less is required to provide effective amounts in the body.

Pharmaceutical compositions according to the present invention include the coated insoluble absorbent which is administered in a slurry or suspension in a pharmaceutically acceptable liquid, as well as capsules, tablets, and dragees containing the coated insoluble absorbent and any optional active ingredients. Preferably, the compositions are those which can be administered orally, and contain from about 0.001 to about 99 percent, preferably from about 0.05 to about 25 percent by weight of active ingredients, together with the coated insoluble absorbent.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying out various disclosed functions may take a variety of alternative forms without departing from the invention. Thus the expressions "means to . . . " and "means for . . . "as may be found in the specification above and/or in the claims below, followed by a functional statement, are intended to define and cover whatever structural, physical, chemical or electrical element or structure may now or in the future exist for carrying out the recited function, whether or not precisely equivalent to the embodiment or embodiments disclosed in the specification above; and it is intended that such expressions be given their broadest interpretation.

What is claimed is:

1. A composition for treating the gastrointestinal tract comprising a powder composition comprising a porous insoluble absorbent selected from the group consisting of charcoal and clay in which the pores of the insoluble absorbent are clogged by a coating material selected from the group consisting of dimethylpolysiloxane and isopropyl myristate, whereby the insoluble absorbent adheres to the gastrointestinal lining, and wherein the ratio of the porous insoluble absorbent to the coating material is from about 3:2 to about 4:1.

2. The composition according to claim 1 further comprising at least one active ingredient.

3. The composition according to claim 2 wherein the active ingredient is selected from the group consisting of antacids, antibiotics, antiseptics, platelet inhibitors, antispasmodics, soporifics, and mixtures thereof.

4. The composition according to claim 2 wherein the active ingredient comprises from about 0.05% to about 80% by weight of the composition.

5. The composition according to claim 4 wherein the ratio of the porous insoluble absorbent to the coating material is about 3:1 by weight.

6. The composition according to claim 3 wherein the active ingredient is an antacid.

7. The composition according to claim 6 wherein the antacid is magnesium oxide.

8. The composition according to claim 6 further containing an antibacterial, antiseptic, or mixtures thereof effective against *Helicobacter pylori*.

9. A method for treating the gastrointestinal tract comprising administering to a patient in need thereof effective amount for treating the gastrointestinal tract of a powder composition comprising a porous insoluble absorbent selected from the group consisting of charcoal and clay in which the pores of the insoluble absorbent are clogged by a coating material selected from the group consisting of isopropyl myristate and dimethypolysiloxane, whereby the insoluble absorbent adheres to the gastrointestinal lining, and the ratio of the porous insoluble absorbent to the coating material is from abour 3:2 to about 4:1.

10. A method for treating gastrointestinal ulcers comprising administering to a patient in need thereof an effective amount for treating ulcers of a composition in powder form comprising a porous insoluble adsorbent selected from the group consisting of clay and charcoal in which the pores of the insoluble absorbent are clogged by a coating material selected from the group consisting of isopropyl myristate and dimethylpolysiloxane, whereby the insoluble absorbent adheres to the gastrointestinal lining, and the ratio of the porous insoluble absorbent to the coating material is from about 3:2 to about 4:1, and said composition further including at least one antacid and at least one compound selected from the group consisting of antibacterials, antiseptics, and mixtures thereof effective against *Helicobacter pylon*.

11. A method for delivering at least one active ingredient to the gastrointestinal tract whereby the therapeutic agent is retained in the gastrointestinal tract comprising administering to a patient in need thereof a composition in powder form comprising a porous insoluble absorbent selected from the group consisting of clay and charcoal containing at least one active ingredient, wherein the pores of the insoluble absorbent are clogged by a coating material selected from the group consisting of isopropyl myristate and dimethylpolysiloxane, and wherein the ratio of the porous insoluble absorbent to the coating material is from about 3:2 to about 4:1.

12. The method according to claim 11 wherein said at least one active ingredient is selected from the group consisting of antacids, antibiotics, antiseptics, platelet inhibitors, antispasmodics, soporifics, and mixtures thereof.

13. The method according to claim 11 wherein the at least one active ingredient comprising from about 0.05% to about 80% by weight of the composition.

14. The method according to claim 12 wherein the ratio of the porous insoluble absorbent to the coating material is from about 3:2 to about 4:1.

15. The method according to claim 9 wherein the porous insoluble absorbent is clay.

16. The method according to claim 10 wherein the porous insoluble absorbent is clay.

17. The method according to claim 11 wherein the porous insoluble absorbent is clay.

18. The method according to claim 12 wherein the porous insoluble absorbent is clay.

19. The method according to claim 13 wherein the porous insoluble absorbent is clay.

20. The method according to claim 14 wherein the porous insoluble absorbent is clay.

21. The method according to claim 9 wherein the porous insoluble absorbent is charcoal.

* * * * *